(12) United States Patent
Ashe

(10) Patent No.: US 8,994,366 B2
(45) Date of Patent: Mar. 31, 2015

(54) MAGNETICALLY TRACKED SENSOR

(71) Applicant: Ascension Technology Corporation, Milton, VT (US)

(72) Inventor: Westley S. Ashe, Hinesburg, VT (US)

(73) Assignee: Ascension Technology Corporation, Shelburne, VT (US)

( * ) Notice: Subject to any disclaimer, the term of this patent is extended or adjusted under 35 U.S.C. 154(b) by 240 days.

(21) Appl. No.: 13/712,105

(22) Filed: Dec. 12, 2012

(65) Prior Publication Data

US 2014/0159707 A1 Jun. 12, 2014

(51) Int. Cl.
*H01F 41/02* (2006.01)
*A61B 19/00* (2006.01)

(52) U.S. Cl.
CPC ........... *H01F 41/02* (2013.01); *Y10T 29/49073* (2015.01); *A61B 19/5244* (2013.01); *A61B 2019/5251* (2013.01); *A61B 2019/5276* (2013.01); *A61B 2019/5289* (2013.01); *A61B 2019/5458* (2013.01)
USPC .................................................. 324/207.16

(58) Field of Classification Search
CPC .......... G01B 7/14; G01B 7/003; H01F 41/02; G01R 33/00; A61B 5/062; A61B 2019/5276; A61B 2019/5251; A61B 19/5244
USPC .............. 324/207.15, 207.16, 253, 256–258, 324/150, 151 A, 342, 388, 546; 29/606
See application file for complete search history.

(56) References Cited

U.S. PATENT DOCUMENTS

| | | | |
|---|---|---|---|
| 3,439,264 A | | 4/1969 | Schonstedt |
| 4,905,698 A | * | 3/1990 | Strohl et al. ................... 600/424 |
| 5,386,828 A | * | 2/1995 | Owens et al. ................. 600/585 |
| 5,469,058 A | | 11/1995 | Dunnam |
| 6,069,475 A | | 5/2000 | Isomura et al. |
| 6,364,823 B1 | * | 4/2002 | Garibaldi et al. ............... 600/12 |
| 2001/0029792 A1 | | 10/2001 | Garshelis |
| 2007/0167879 A1 | | 7/2007 | Cochran |
| 2011/0152721 A1 | * | 6/2011 | Sela et al. ..................... 600/585 |
| 2012/0130228 A1 | | 5/2012 | Zellers et al. |

OTHER PUBLICATIONS

International Search Report and Written Opinion, PCT/US2013/074705, mailed May 12, 2014, 8 pages.

* cited by examiner

*Primary Examiner* — Tung X Nguyen
*Assistant Examiner* — Son Le
(74) *Attorney, Agent, or Firm* — Fish & Richardson P.C.

(57) ABSTRACT

A magnetic field sensor assembly includes a hollow cylindrical core, conductive material and at least first and second lead wires. The hollow cylindrical core is made of ferromagnetic material and has a proximal end and a distal end. The conductive material is disposed around the hollow cylindrical core and forms at least one turn of a coil that has at least one start terminal and at least one finish terminal. The first and second lead wires pass through the center of the hollow cylindrical core and the first lead wire is connected to the start terminal thereby forming a first termination and the second lead wire is connected to the finish terminal thereby forming a second termination. The first and second terminations are positioned within the hollow cylindrical core.

30 Claims, 6 Drawing Sheets

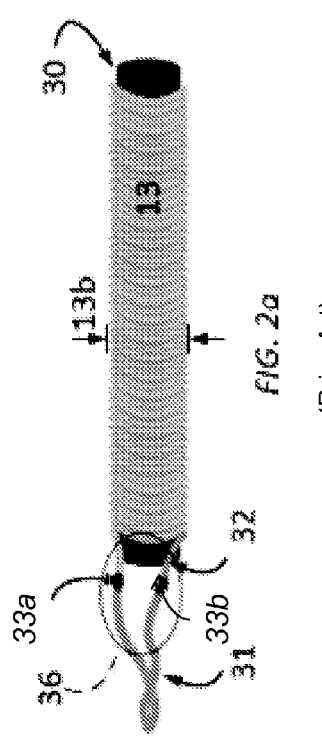
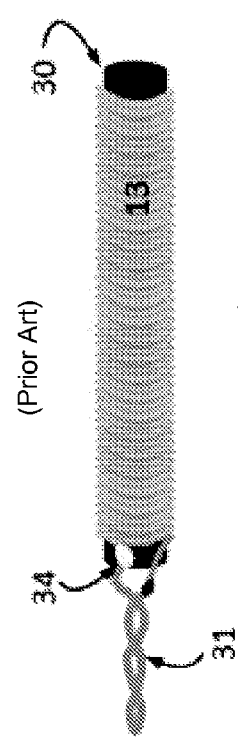
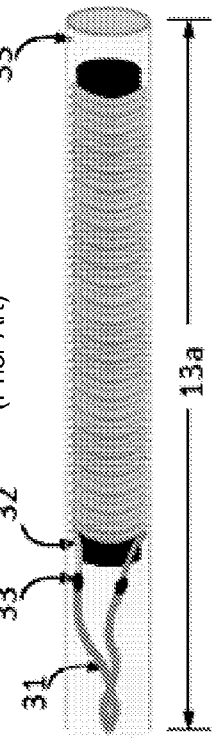
FIG. 2a (Prior Art)
FIG. 2b (Prior Art)
FIG. 2c (Prior Art)

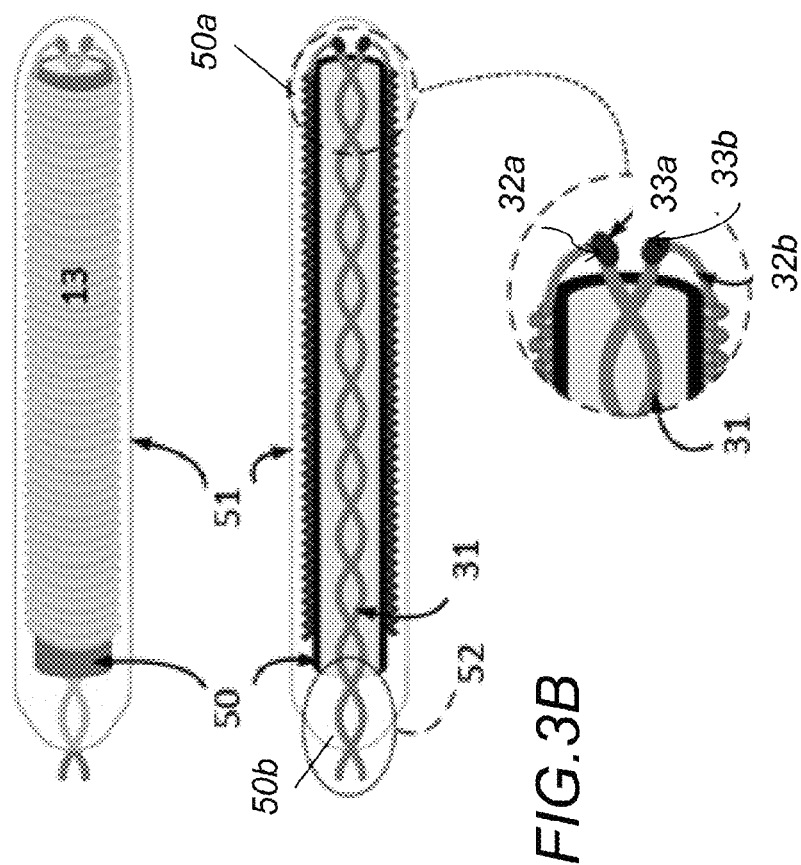

MAGNETICALLY TRACKED SENSOR

TECHNICAL FIELD

This disclosure relates to a magnetically tracked sensor.

BACKGROUND

Magnetic tracking of instruments with respect to imaged anatomy is widely employed in medical practice. Imaging systems that are enhanced with magnetic tracking may be used to track and display position and orientation of a diagnostic or therapeutic instrument relative to the imaging plane. They can help the clinician guide the instrument to a chosen target with reduced error compared to an unguided instrument. Furthermore, the visual representation of the tracked instrument is not necessarily constrained to the ultrasound imaging plane, thus enabling the clinician with more freedom of motion.

For magnetic tracking of an instrument, an electromagnetic sensor can be included in a location of the instrument. Electromagnetic sensors can be electromagnetic coils that surround or are close to the objects whose location is being tracked. If an instrument with an included sensor is placed within a varying electromagnetic field, a voltage can be generated in the electromagnetic sensor. This generated voltage can be used to determine and track the locations and relative positioning of the instrument within the electromagnetic field. An ultrasound system enhanced with magnetic tracking of sensors can display a 3-dimensional merger of ultrasound generated anatomical features and the visual representation of the instrument position and orientation.

SUMMARY

In one aspect, in general, a magnetic field sensor assembly includes a hollow core comprising a ferromagnetic material, the hollow core having a proximal end and a distal end, conductive material disposed around the hollow core and forming at least one turn of a coil, the coil comprising at least one start terminal and at least one finish terminal, at least first and second lead wires passing through the center of the hollow core, wherein the first lead wire is connected to the start terminal to form a first termination and wherein the second lead wire is connected to the finish terminal to form a second termination, and wherein the first and second lead wires are capable of carrying electrical signals from the coil to a magnetic position measurement system for determining a sensor position.

Implementations may include one or more of the following features. The hollow core is a hollow cylindrical core. The first and second terminations are positioned within the hollow core. The first and second terminations are positioned within the distal end of the hollow core. The first and second terminations are positioned within the proximal end of the hollow core. The first and second lead wires and the first and second terminations are permanently fixed within the hollow core. The hollow core includes ferrite material. The hollow core includes magnetic material. The hollow core includes hardened austenitic stainless steel material. The conductive material includes magnetic wire. The conductive material includes patterned conductive material deposited onto a dielectric material. The first and second terminations are formed by soldering, welding or joining by a conductive adhesive.

In another aspect, in general, a method includes providing a hollow core comprising ferromagnetic material, the hollow core having a proximal end and a distal end, disposing conductive material around the hollow core and forming at least one turn of a coil, the coil comprising at least one start terminal and at least one finish terminal, passing at least first and second lead wires through the center of the hollow core, connecting the first lead wire to the start terminal to form a first termination, connecting the second lead wire to the finish terminal to form a second termination, wherein the first and second lead wires are capable of carrying electrical signals from the coil to a magnetic position measurement system for determining a sensor position.

Implementations may include one or more of the following features. The hollow core is a hollow cylindrical core. The first and second terminations are positioned within the hollow core. The first and second terminations are positioned within the distal end of the hollow core. The first and second terminations are positioned within the proximal end of the hollow core. The method includes permanently fixing the first and second lead wires and the first and second terminations within the hollow core. The hollow core includes ferrite material. The hollow core includes magnetic material. The hollow core includes hardened austenitic stainless steel material. The conductive material includes magnetic wire. The conductive material includes patterned conductive material deposited onto a dielectric material. The first and second terminations are formed via soldering, welding or joining via a conductive adhesive.

In a further aspect, in general, an electromagnetic position measurement system includes a magnetic field sensor assembly configured to measure at least 3 degrees of freedom position and angular orientation data when placed within an electromagnetic field and including a hollow core comprising a ferromagnetic material, the hollow core having a proximal end and a distal end, conductive material disposed around the hollow core and forming at least one turn of a coil, the coil comprising at least one start terminal and at least one finish terminal, and at least first and second lead wires passing through the center of the hollow core, wherein the first lead wire is connected to the start terminal to form a first termination and wherein the second lead wire is connected to the finish terminal to form a second termination, wherein the first and second terminations are positioned within the hollow core and wherein the first and second lead wires are capable of carrying electrical signals from the coil to the electromagnetic position measurement system for determining a sensor position.

Implementations may include one or more of the following features. The hollow core is a hollow cylindrical core. The first and second terminations are positioned within the hollow core.

Two or more of the features described in this disclosure, including those described in this summary section, may be combined to form implementations not specifically described herein.

The details of one or more implementations are set forth in the accompanying drawings and the descriptions below. Other features, objects, and advantages will be apparent from the description and drawings, and from the claims.

DESCRIPTION OF DRAWINGS

FIG. 2A-FIG. 2C illustrate methods of attachment and encapsulation of the sensor element.

FIG. 3A-FIG. 3C depict cross-sectional views of a hollow ferromagnetic core sensor.

Like reference symbols in the various drawings indicate like elements.

DETAILED DESCRIPTION

Figure 1:
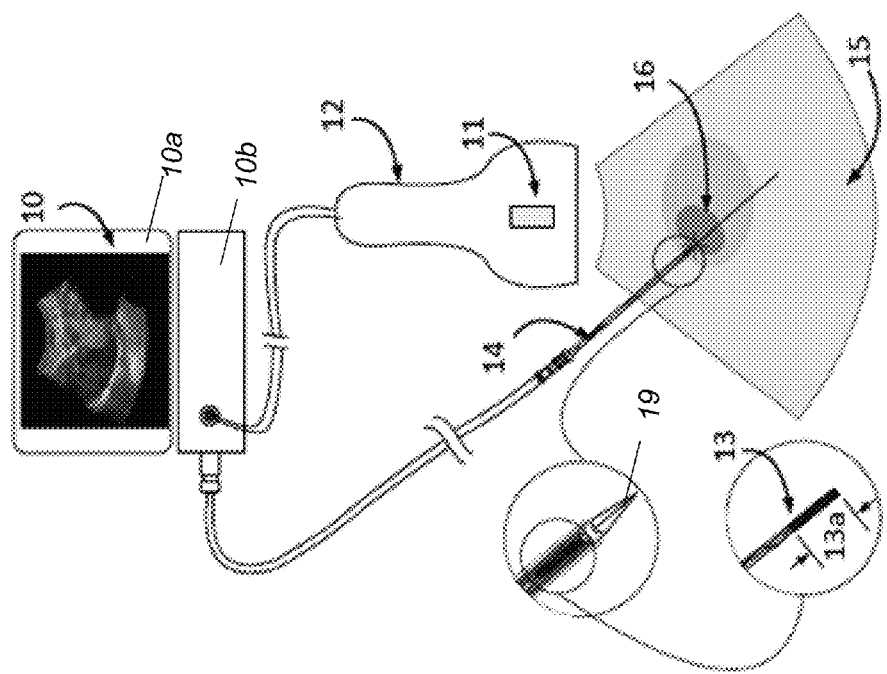
FIG. 1 illustrates an ultrasound imaging system enhanced with magnetic instrument tracking.

Referring to FIG. 1, imaging tools, such as ultrasound system 10, are used to image detailed anatomical features in a spatial slice (or imaging plane) 16. Ultrasound system 10 includes a hand-held probe 12, a display 10a and electronics 10b. For magnetic tracking of an instrument 14 with ultrasound system 10, electromagnetic sensors 11 and 13 are included in the hand-held ultrasound probe 12 and in a location of instrument 14, respectively. Sensors 11 and 13 can be electromagnetic coils that surround or are close to the objects whose location is being tracked. In the example of FIG. 1, instrument 14 is a needle assembly and sensor 13 is close to the needle tip 19. When sensor 13 is placed within a varying electromagnetic field, a voltage is generated in the electromagnetic sensor 13. Similarly, when hand-held ultrasound probe 12 with the embedded sensor 11 is placed within the varying electromagnetic field, a voltage is generated in the electromagnetic sensor 11. These generated voltages in sensors 11, 13 are used to determine and track the locations and relative positioning of ultrasound probe 12 and needle tip 19, respectively, within the electromagnetic field. Ultrasound system 10, enhanced with magnetic tracking of sensors 11 and 13, displays the 3-dimensional merger of ultrasound generated anatomical features 16 in area of interest 15 and the visual representation of the instrument's 14 position and orientation.

FIGS. 2A-2C show two methods of constructing five degree-of-freedom magnetic sensor assemblies. Magnet wire 32 is wound around ferromagnetic core 30. In FIG. 2A, lead wire pair 31 is connected to magnet wires 32 at each of two termination (winding start and finish) points 33a, 33b. The finished diameter 13b of sensor 13 is usually in the range of 1 mm, and may be as small as 0.3 mm, so the components, especially the connection points 33a, 33b, are extremely fragile and difficult to manipulate without damaging them. These construction methods result in a very fragile zone between termination points 33a, 33b and core 30, as coil wire 32 is typically 0.0005" in diameter and is thus easily damaged or broken. In certain cases, it is advantageous to join one conductor of lead wire 31 directly to core 30 by soldering or adhesive methods 34, as shown in FIG. 2B. This allows the larger conductor of lead wire 31 to support the mechanical forces encountered by sensor 13 during assembly and use. This joining process has the disadvantage of requiring precise application and curing of adhesive or subjecting the coil assembly to soldering temperatures, which may damage the insulation if not done precisely. A second common method of addressing the fragility of termination area 33 is to place a tube 35 over the sensor 13, such that it encompasses termination area 33 and provides mechanical support. The tube 35 with sensor 13 assembly is then fill-injected with adhesive. This tube must extend well beyond termination area 33 to provide overlap between the lead wires and the tube, allowing area for the lap shear adhesive joint to form. This has the disadvantage of either increasing the rigid length 13a of sensor 13 or requiring a shorter core, which will decrease the signal output of the sensor and reduce its useful range. The methods of adhesive injection require costly sensor-to-tube alignment fixturing and precise flow controllers. Also, the rigid nature of tube 35 and the extended lap shear area form a lever arm with the weak point at termination area 33. Great care must be taken during the assembly process not to break or damage connection wires 31 32 or termination points 33a, 33b when inserting them into tube 35. Tube 35 is commonly a metal material such as stainless steel or a plastic material such as polyester, depending on the desired properties of the finished product. When tube 35 is a plastic material, it must have enough wall thickness to prevent flexing of termination area 33, as the connections in this area are easily broken. Although tube 35 is commonly filled with a stress relieving adhesive, termination area 33 is still a weak stress point and is prone to breakage. Also, the termination of these sensors is exposed to the magnetic field, which the sensors are detecting. Since a single coil sensor cannot detect rotation about its axis, it must be assumed that the magnetic axis and physical axis of the coil are co-linear. If the termination process results in an undesired out of plane loop 36 being formed. This loop 36 may misalign the sensor's 13 magnetic axis from its physical axis. Such a loop is in fact very difficult to avoid in some construction methods as the conductors are separated in the termination area 33 to avoid short circuiting, and a relatively large loop results from this separation.

Referring to FIGS. 3A-3C, ferromagnetic sensor 13 includes a twisted lead wire 31 placed within a ferromagnetic hollow core 50. Coil wire 32 is wound around the ferromagnetic core 50 and the ends 32a, 32b are connected to the termination ends 33a, 33b of the lead wire 31, which occurs at the opposite end of core 50, compared to the sensors shown in FIGS. 2A-2C. Adhesive coating 51 is applied after completing termination connections 33a, 33b and is wicked into the space between core 50 and lead wire 31, thus creating a secure bond along the inside surface of core 50. Terminations 33a, 33b can be performed in close proximity to the end 50a of core 50 so as to minimize the length of the sensor 13. Because the bonding surfaces between lead wire 31 and coil wire 32 are internal to core 50, strain relief area 52 can be zero length, which is not possible with other construction techniques. This allows the rigid portion of the sensor to be shorter without sacrificing the strength of the assembly, thus enabling instruments equipped with the sensor to navigate tortuous anatomy, such as blood vessels, more easily.

As was shown in FIG. 2A, in one sensor design, coil wire 32 and lead wire 31 are sometimes deformed during the termination process. This deformation is difficult to avoid as lead wire 31 must be separated somewhat so that it can be joined to coil wires 32 at termination 33 without creating a short circuit caused by the removal of insulation in the area of termination 33. Also, some bending and manipulation of coil wires 32 and lead wires 31 is usually required. Due to these factors, a small undesired parasitic loop 36 can be formed. This loop has an axis of maximum sensitivity which may differ from the physical axis of sensor 13. Shielding this loop's magnetic field can remove the effect of the loop on the sensor output.

Figure 4A:
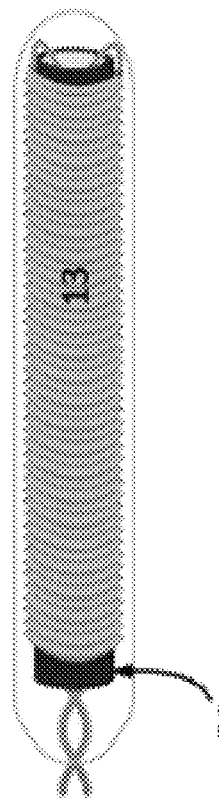
FIG. 4A-FIG. 4C depict cross-sectional views of another implementation of a hollow ferromagnetic core sensor.
Figure 4B:
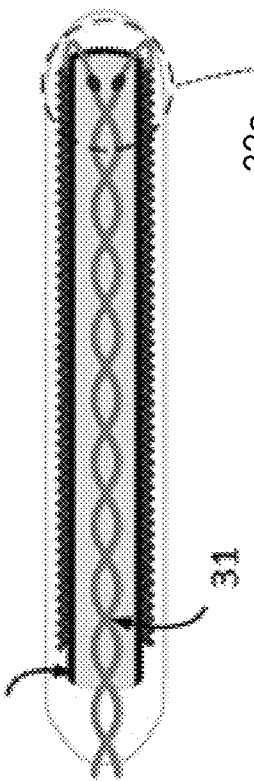
Figure 4C:
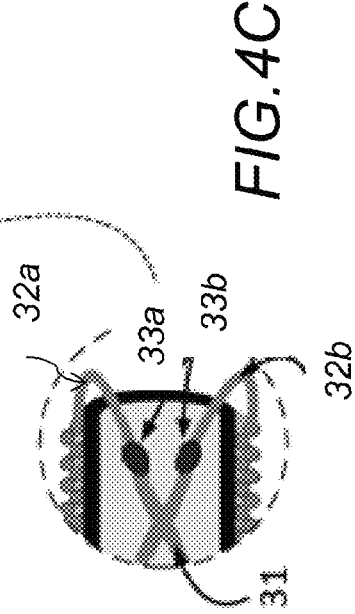

Referring to FIGS. 4A-4C, in a method of aligning the magnetic and physical axes of sensor 13, terminations 33a, 33b are connected to coil wire ends 32a, 32b at the distal end 50a of core 50 and then the connected termination points are inserted into the distal end 50a of core 50 and pushed towards into the hollow core 50. Because the magnetic field inside of a ferromagnetic tube is attenuated, core 50 acts as a magnetic shield for undesired parasitic loops formed during the creation of terminations 33a, 33b. This has a benefit of improving the alignment of the magnetic and physical axes of sensor 13. The alignment of the magnetic and physical axes of sensor 13 is notable because sensor 13 cannot detect angular rotation parallel to its magnetic axis, thus if the magnetic and physical axes of sensor 13 are not co-incident, imaging errors occur. Therefore, if the magnetic and physical axes are not aligned, sliding sensor 13 into a biopsy needle such as tubular instrument 14 causes errors in the displayed trajectory of instrument 14 with respect to imaged anatomy 10. A calibration step may be employed to reduce this trajectory error, but this complicates the manufacturing process. Placing terminations 33a, 33b inside of core 50 removes a major source of error for applications requiring accurate display of instrument trajectory without additional calibration steps.

Figure 5A:
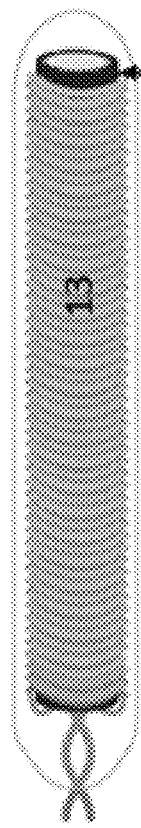
FIG. 5A-FIG. 5C depict cross-sectional views of yet another implementation of a hollow ferromagnetic core sensor.
Figure 5B:
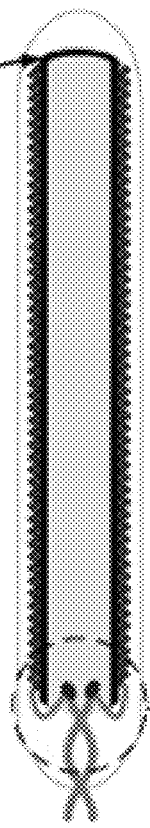
Figure 5C:
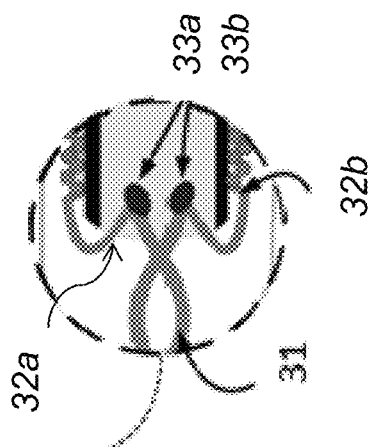

In certain applications, it may not be possible to gain access to the distal end 50a of hollow core 50. This is the case when sensor 13 is pre-molded into an instrument with only the proximal end 50b of core 50 exposed. In this case, referring to FIGS. 5A-5C, terminations 33a, 33b are performed at the proximal end 50b of core 50. The ends 32a, 32b of lead cable 31 are connected to terminations 33a, 33b and the connected points are inserted into proximal end 50b and pushed within the hollow core 50. Core 50 then acts as a magnetic shield for terminations 33a, 33b, and the improvements in imaging accuracy are similar to those gained by shielding terminations 33a, 33b at the distal end 50b of core 50.

Figure 6:
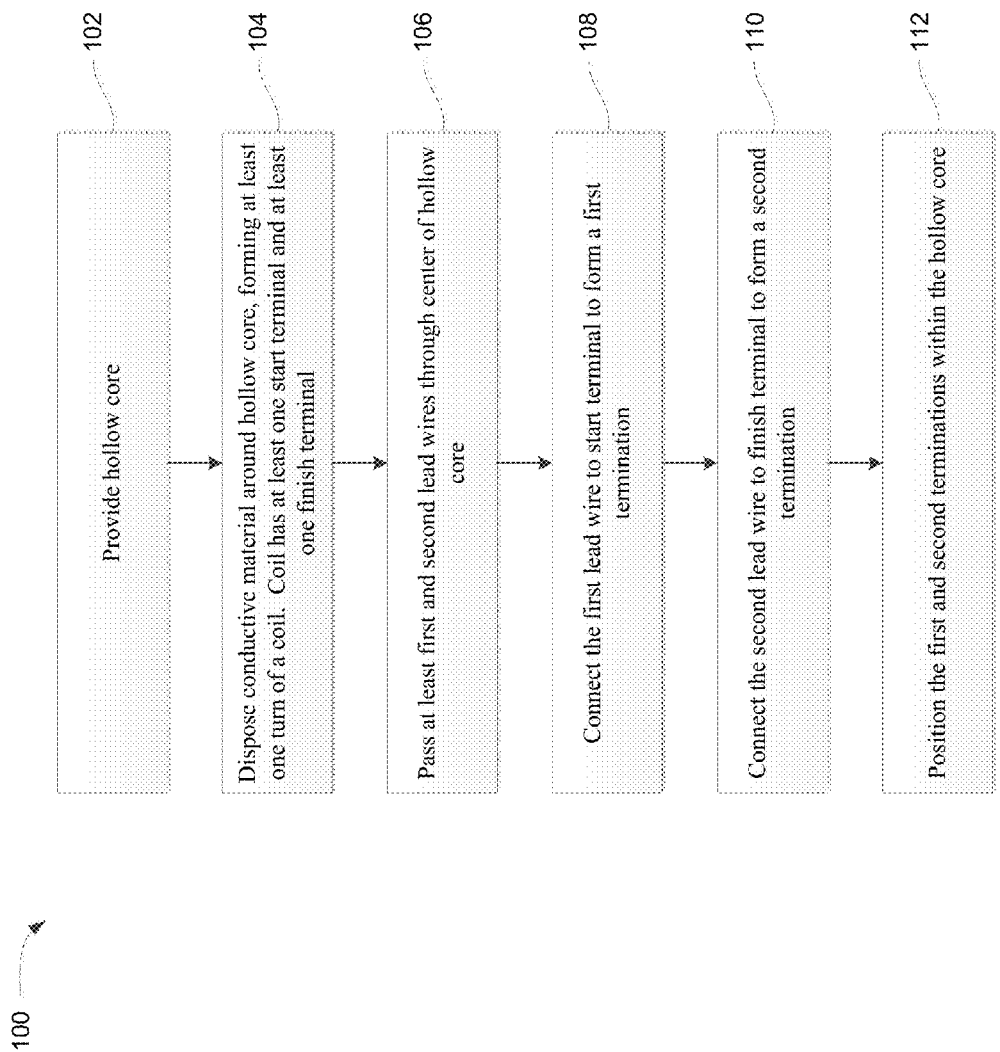
FIG. 6 shows a flowchart detailing steps for producing a magnetic field sensor assembly.

FIG. 6 shows a flowchart 100 detailing steps for producing a magnetic field sensor assembly, e.g., the magnetic field sensor assembly shown in FIGS. 3A-3C. Step 102 includes providing a hollow core (e.g., a hollow cylindrical core) comprising ferromagnetic material. The hollow core has a proximal end and a distal end. In some implementations, the hollow core can include ferrite material. The hollow core can also include magnetic material. In some examples, the hollow core can include hardened austenitic stainless steel material. Step 104 includes disposing conductive material around the hollow core and forming at least one turn of a coil. The coil has at least one start terminal and at least one finish terminal. In some implementations, the conductive material can include magnetic wire. In some implementations, the conductive material can include patterned conductive material deposited onto a dielectric material. Step 106 includes passing first and second lead wires through the center of the hollow core. Step 108 includes connecting the first lead wire to the start terminal to form a first termination. Step 110 includes connecting the second lead wire to the finish terminal to form a second termination. In some examples, the first and second terminations can be positioned within the distal end or the proximal end of the hollow core. In some implementations, the first and second lead wires and the first and second terminations can be permanently fixed within the hollow core. Step 112 includes optionally positioning the first and second terminations within the hollow core. The first and second lead wires can be capable of carrying electrical signals from the coil to a magnetic position measurement system for determining a sensor position.

The magnetic field sensor assembly described here tends to have a termination area that is less fragile than other kinds of sensors. Various implementations of the assembly are possible. The ferromagnetic core can be made hollow, an example being a ferrite bead core. The lead wire can be passed through the center of the hollow bead core, and can be secured with an adhesive tack before performing the delicate process of connecting the fragile coil wires to the lead wire. The termination process can be performed at the distal end of the assembly. The application of adhesive can be done on the proximal end of the coil and is much simpler because capillary action will pull the adhesive into the center of the hollow core in a controllable manner.

In some examples, the sensor can be dipped in adhesive, whereby the adhesive wicks into and around the sensor, securing any wires inside the core and encapsulating the sensor. The self fixturing nature of this process can allow the termination process to proceed without maintaining the coil assembly and lead wire in a fixed location relative to each other. Positioning terminations on the distal end or inside the sensor core also shortens the sensor for a given core length, as the lead wires are strain relieved to the inside of the core. A lever arm with the highest stress point coinciding with the weakest point over the termination area need not be used.

The termination can be performed at the distal or proximal end without first securing the lead wire to the inside of the hollow sensor core. The termination can be pushed or pulled into the hollow core before applying adhesive. In this manner, the termination area does not add to the length of the sensor, and the lead wire can still be securely fastened to the inside of the sensor core. In this configuration, the parasitic loops formed by the terminations are magnetically shielded by the hollow core and the magnetic axis of the sensor is better aligned with the physical axis.

The magnetic sensor may be movable within the instrument in order to enable its replacement with a therapeutic device after successful placement of the instrument tip at the target area. Furthermore, the magnetic sensor may be re-introduced for the purpose of navigating to another target. The magnetic sensor can be constructed so that it can handle this movement. Also, due to the curvilinear nature of many surgical tools and of most passages in the human body, the length of the magnetic sensor can be limited while maintaining its mechanical strength.

Other implementations not specifically described herein are also within the scope of the following claims.

I claim:
1. A magnetic field sensor assembly comprising:
a hollow core comprising a ferromagnetic material, the hollow core having a proximal end and a distal end;
conductive material disposed around the hollow core and forming at least one turn of a coil, the coil comprising at least one start terminal and at least one finish terminal; and
at least first and second lead wires passing through the hollow portion of the hollow core, wherein the first lead wire is connected to the start terminal to form a first termination and wherein the second lead wire is connected to the finish terminal to form a second termination, and wherein the first and second lead wires are capable of carrying electrical signals from the coil to a magnetic position measurement system for determining a sensor position,
thereby reducing fragility of the sensor assembly.
2. The assembly of claim 1 wherein the hollow core is a hollow cylindrical core.
3. The assembly of claim 1 wherein the first and second terminations are positioned within the hollow core.
4. The assembly of claim 3 wherein the first and second terminations are positioned within the distal end of the hollow core.
5. The assembly of claim 3 wherein the first and second terminations are positioned with the proximal end of the hollow core.
6. The assembly of claim 3 wherein the first and second terminations are permanently fixed within the hollow core.

7. The assembly of claim 1 wherein the hollow core comprises ferrite material.

8. The assembly of claim 1 wherein the hollow core comprises magnetic material.

9. The assembly of claim 1 wherein the hollow core comprises hardened austentic stainless steel material.

10. The assembly of claim 1 wherein the material comprises magnetic wire.

11. The assembly of claim 1 wherein the conductive material comprises patterned conductive material deposited onto a dielectric material.

12. The assembly of claim 1 wherein the first and second terminations are formed by soldering, welding or joining by a conductive adhesive.

13. The assembly of claim 1 wherein the hollow core acts as a magnetic shield for loops formed by either or both of the first termination and the second termination.

14. A method comprising:
providing a hollow core comprising ferromagnetic material, the hollow core having a proximal end and a distal end;
disposing conductive material around the hollow core and forming at least one turn of a coil, the coil comprising at least one start terminal and at least one finish terminal;
passing at least first and second lead wires through the hollow portion of the hollow core;
connecting the first lead wire to the start terminal to form a first termination; and
connecting the second lead wire to the finish terminal to form a second termination, thereby reducing fragility of the sensor assembly;
wherein the first and second lead wires are capable of carrying electrical signals from the coil to a magnetic position measurement system for determining a sensor position.

15. The method of claim 14 wherein the hollow core is a hollow cylindrical core.

16. The method of claim 14 wherein the first and second terminations are positioned within the hollow core.

17. The method of claim 16 wherein the first and second terminations are positioned within the distal end of the hollow core.

18. The method of claim 16 wherein the first and second terminations are positioned within the proximal end of the hollow.

19. The method of claim 16 further comprising permanently fixing the first and second lead wires and the first and second terminations within the hollow core.

20. The method of claim 14 wherein the hollow core comprises ferrite material.

21. The method of claim 14 wherein the hollow core comprises magnetic material.

22. The method of claim 14 wherein the hollow core comprises hardened austenitic stainless steel material.

23. The method of claim 14 wherein the conductive material comprises magnetic wire.

24. The method of claim 14 wherein the conductive material comprises patterned conductive material deposited onto a dielectric material.

25. The method of claim 14 wherein the first and second terminations are formed via soldering, welding or joining via a conductive adhesive.

26. The method of claim 14 wherein the hollow core acts as a magnetic shield for loops formed by either or both of the first termination and the second termination.

27. An electromagnetic position measurement system comprising:
a magnetic field sensor assembly configured to measure at least three degrees of freedom position and angular orientation data when placed within an electromagnetic field and comprising:
a hollow core comprising a ferromagnetic material, the hollow core having a proximal end and a distal end;
conductive material disposed around the hollow core and forming at least one turn of a coil, the coil comprising at least one start terminal and at least one finish terminal; and
at least first and second lead wires passing through the hollow portion of the hollow core, wherein the first lead wire is connected to the start terminal to form a first termination and wherein the second lead wire is connected to the finish terminal to form a second termination, and wherein the first and second lead wires are capable of carrying electrical signals from the coil to the electromagnetic position measurement system for determining a sensor position,
thereby reducing fragility of the sensor assembly.

28. The system of claim 27 wherein the hollow core is a hollow cylindrical core.

29. The system of claim 27 wherein the first and second terminations are positioned within the hollow core.

30. The system of claim 27 wherein the hollow core acts as a magnetic shield for loops formed by either or both of the first termination and the second termination.

* * * * *

UNITED STATES PATENT AND TRADEMARK OFFICE
CERTIFICATE OF CORRECTION

| | | |
|---|---|---|
| PATENT NO. | : 8,994,366 B2 | Page 1 of 1 |
| APPLICATION NO. | : 13/712105 | |
| DATED | : March 31, 2015 | |
| INVENTOR(S) | : Westley S. Ashe | |

It is certified that error appears in the above-identified patent and that said Letters Patent is hereby corrected as shown below:

In The Claims

Column 7, Line 6, In Claim 9, delete "austentic" and insert -- austenitic --

Signed and Sealed this
Twenty-second Day of September, 2015

Michelle K. Lee
*Director of the United States Patent and Trademark Office*